United States Patent
Le et al.

(10) Patent No.: US 9,566,072 B2
(45) Date of Patent: Feb. 14, 2017

(54) COIL SYSTEM

(71) Applicant: Blockade Medical, LLC, Irvine, CA (US)

(72) Inventors: Jake Le, Foothill Ranch, CA (US); David Ferrera, Coto De Caza, CA (US); Dawson Le, Garden Grove, CA (US); Randall Takahashi, Mission Viejo, CA (US); George Martinez, Tustin, CA (US)

(73) Assignee: BLOCKADE MEDICAL, LLC, Irvine, CA (US)

( * ) Notice: Subject to any disclaimer, the term of this patent is extended or adjusted under 35 U.S.C. 154(b) by 199 days.

(21) Appl. No.: 14/584,848

(22) Filed: Dec. 29, 2014

(65) Prior Publication Data

US 2015/0182227 A1   Jul. 2, 2015

Related U.S. Application Data

(60) Provisional application No. 61/921,338, filed on Dec. 27, 2013.

(51) Int. Cl.
*A61M 29/00* (2006.01)
*A61B 17/12* (2006.01)
*A61B 17/00* (2006.01)

(52) U.S. Cl.
CPC ... *A61B 17/12113* (2013.01); *A61B 17/12154* (2013.01); *A61B 17/12172* (2013.01); *A61B 2017/00526* (2013.01); *A61B 2017/1205* (2013.01); *A61B 2017/12063* (2013.01)

(58) Field of Classification Search
CPC   A61F 2/01; A61F 2002/016; A61F 2002/011; A61F 2/013; A61F 2230/0067; A61F 2230/008; A61F 2230/0006; A61F 2230/005; A61F 2210/0014; A61F 2230/0076; A61F 2230/0091; A61B 17/12109; A61B 17/12172; A61B 17/12113; A61B 17/12031; A61B 2017/00867; A61B 2017/1205; A61B 17/0057; A61B 17/1214
USPC .......................... 606/191, 194, 200
See application file for complete search history.

(56) References Cited

U.S. PATENT DOCUMENTS

| | | | | |
|---|---|---|---|---|
| 5,354,295 A | * | 10/1994 | Guglielmi | A61B 17/12022 604/907 |
| 6,280,457 B1 | * | 8/2001 | Wallace | A61B 17/12022 606/191 |
| 6,322,576 B1 | * | 11/2001 | Wallace | A61B 17/12022 606/191 |

* cited by examiner

*Primary Examiner* — Katherine M Shi
(74) *Attorney, Agent, or Firm* — Patnstr, APC; Peter Jon Gluck

(57) ABSTRACT

Vaso-impacting implants and novel methods of making coils, stent-trievers, flow diverters and the like enable aneurysm treatment, including in the brain. Refined and variegated framing and complex coils provide for rapid electrolytic detachment, including less than 20 second embodiments. Novel enhanced mandrels, fittings and winding schemes are likewise disclosed improving the standard of care and state of the art.

6 Claims, 9 Drawing Sheets

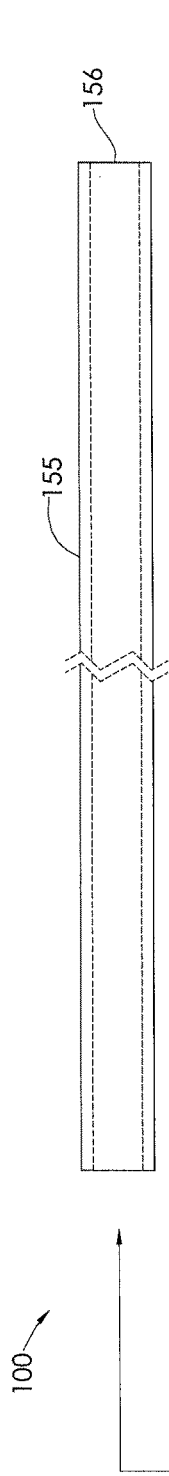
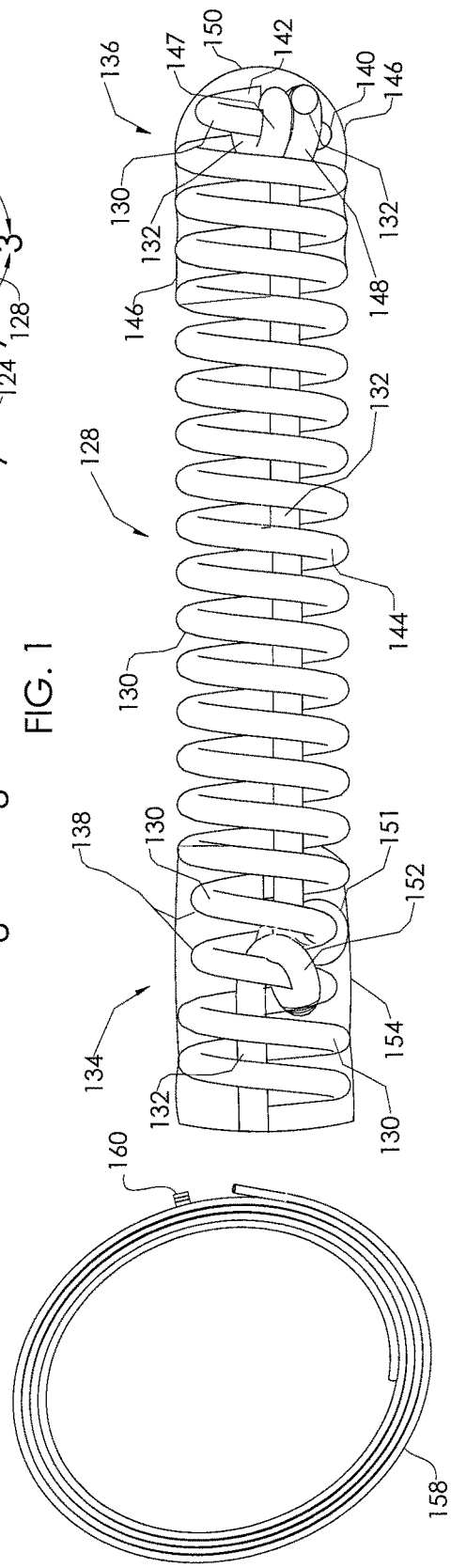
FIG. 1
FIG. 2
FIG. 3

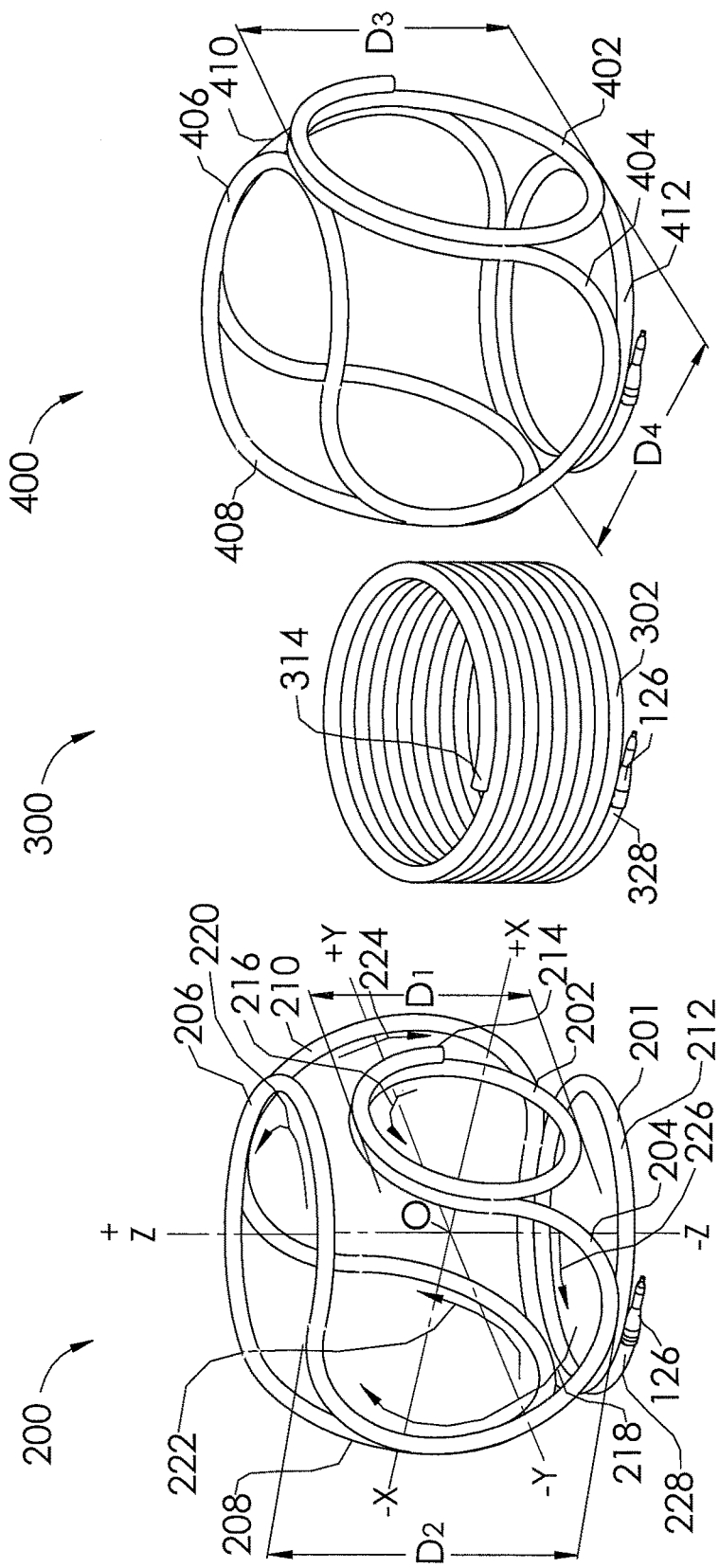

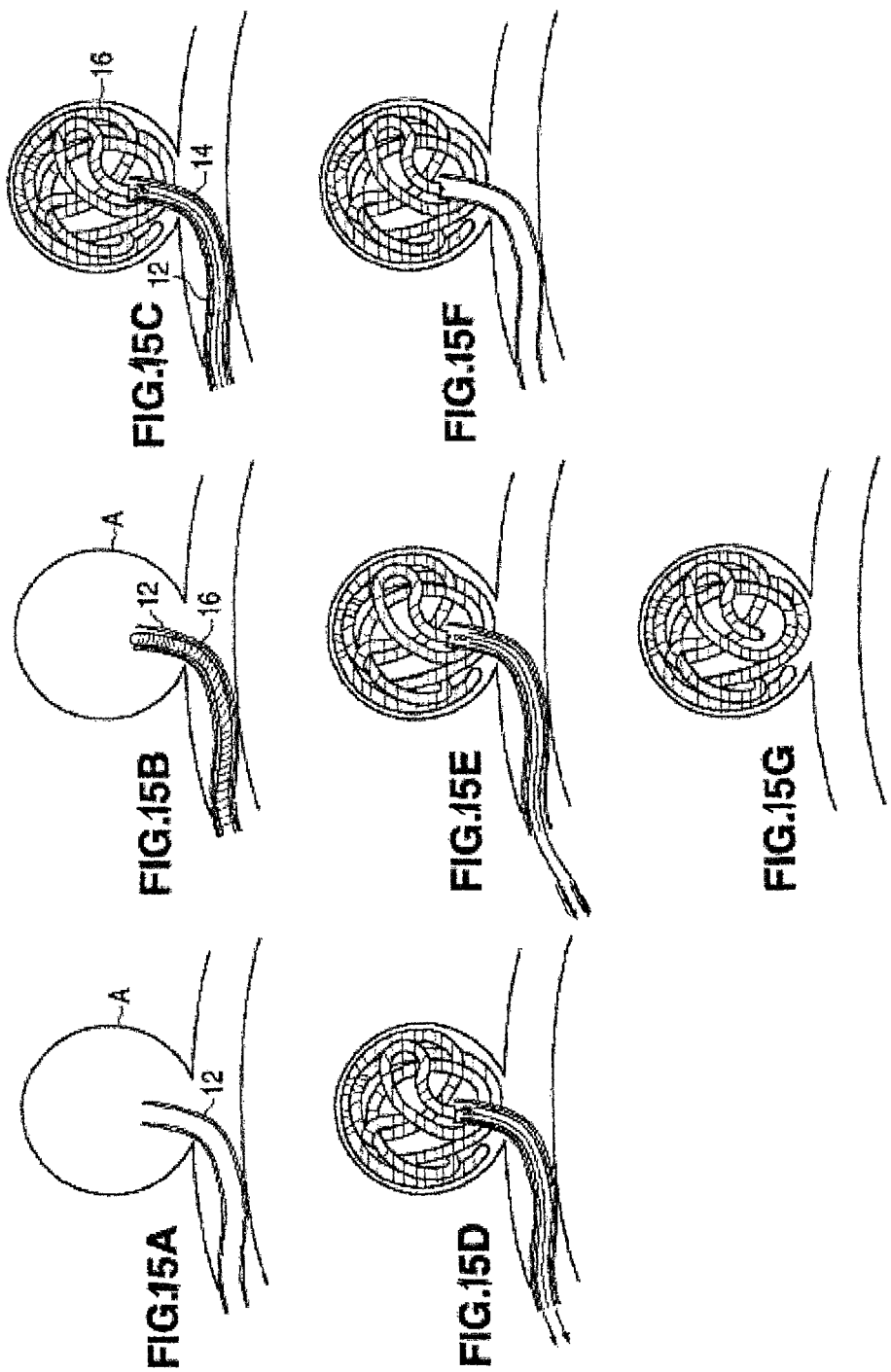

COIL SYSTEM

CROSS-REFERENCE TO RELATED APPLICATIONS

This application claims the benefit of, and priority to, U.S. Provisional Application Ser. No. 61/921,338, filed Dec. 27, 2013, the content of which is incorporated herein by reference herein in its entirety.

FIELD OF THE INVENTION

The field of the invention generally relates to medical devices for the treatment of vascular abnormalities.

BACKGROUND OF THE INVENTION

Hemorrhagic stroke may occur as a result of a subarachnoid hemorrhage (SAH), which occurs when a blood vessel on the brain's surface ruptures, leaking blood into the space between the brain and the skull. In contrast, a cerebral hemorrhage occurs when a defective artery in the brain bursts and floods the surrounding tissue with blood. Arterial brain hemorrhage is often caused by a head injury or a burst aneurysm, which may result from high blood pressure. An artery rupturing in one part of the brain can release blood that comes in contact with arteries in other portions of the brain. Even though it is likely that a rupture in one artery could starve the brain tissue fed by that artery, it is also likely that surrounding (otherwise healthy) arteries could become constricted, depriving their cerebral structures of oxygen and nutrients. Thus, a stroke that immediately affects a relatively unimportant portion of the brain may spread to a much larger area and affect more important structures.

Currently there are two major treatment options for cerebral aneurysm therapy, in either ruptured or unruptured aneurysms. One option is surgical clipping. The goal of surgical clipping is to isolate an aneurysm from the normal circulation without blocking off any small perforating arteries nearby. Under general anesthesia, an opening is made in the skull, called a craniotomy. The brain is gently retracted to locate the aneurysm. A small clip is placed across the base, or neck, of the aneurysm to block the normal blood flow from entering. The clip works like a tiny coil-spring clothespin, in which the blades of the clip remain tightly closed until pressure is applied to open the blades. Clips are made of titanium or other metallic materials and remain on the artery permanently. The second option is neurovascular embolization, which is to isolate ruptured or rupture-prone neurovascular abnormalities including aneurysms and AVMs (arterio-venous malformations) from the cerebral circulation in order to prevent a primary or secondary hemorrhage into the intracranial space.

Cerebrovascular embolization may be accomplished through the transcatheter deployment of one or several embolizing agents in an amount sufficient to halt internal blood flow and lead to death of the lesion. Several types of embolic agents have been approved for neurovascular indications including glues, liquid embolics, occlusion balloons, platinum and stainless steel microcoils (with and without attached fibers), and polyvinyl alcohol particles. Microcoils are the most commonly employed device for embolization of neurovascular lesions, with microcoiling techniques employed in the majority of endovascular repair procedures involving cerebral aneurysms and for many cases involving permanent AVM occlusions. Neurovascular stents may be employed for the containment of embolic coils. Other devices such as flow diversion implants or flow disruptor implants are used in certain types of aneurysms.

Many cerebral aneurysms tend to form at the bifurcation of major vessels that make up the circle of Willis and lie within the subarachnoid space. Each year, approximately 40,000 people in the U.S. suffer a hemorrhagic stroke caused by a ruptured cerebral aneurysm, of which an estimated 50% die within 1 month and the remainder usually experience severe residual neurologic deficits. Most cerebral aneurysms are asymptomatic and remain undetected until an SAH occurs. An SAH is a catastrophic event due to the fact that there is little or no warning and many patients die before they are able to receive treatment. The most common symptom prior to a vessel rupture is an abrupt and sudden severe headache.

Other vascular abnormalities may benefit from treatment with delivery of vascular implants. Aortic aneurysms are commonly treated with stent grafts. A variety of stents are used for the treatment of atherosclerotic, and other diseases of the vessels of the body. Detachable balloons have been used for both aneurysm occlusion and vessel occlusion.

BRIEF DESCRIPTION OF THE DRAWINGS

FIG. 1 is a side elevation view of a vasoocclusive implant system according to an embodiment of the present invention.

FIG. 2 is a perspective view of a protective shipping tube for the vasoocclusive implant system of FIG. 1.

FIG. 3 is a detailed view of a distal tip portion of the vasoocclusive implant system of FIG. 1, taken from within circle 3.

FIG. 4 is a perspective view of a vasoocclusive implant according to one embodiment of the invention.

FIG. 5 is a perspective view of a vasoocclusive implant according to another embodiment of the invention.

FIG. 6 is a perspective view of a vasoocclusive implant according to another embodiment of the invention.

FIGS. 15A-15G are a sequence of drawings schematically illustrating the steps of occluding an aneurysm using the vasoocclusive implant systems of FIGS. 1-14.

DETAILED DESCRIPTION OF THE ILLUSTRATED EMBODIMENTS

Figure 7:
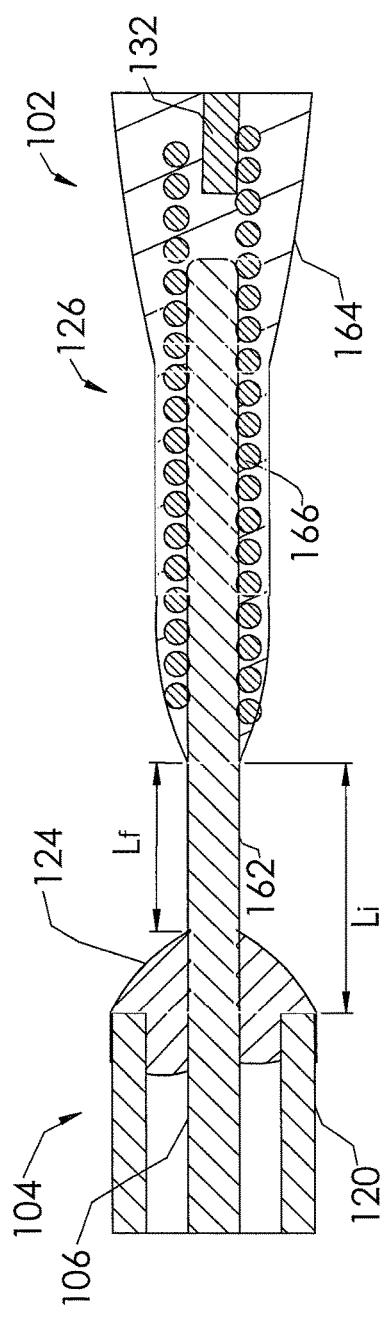
FIG. 7 is a sectional view of FIG. 1, taken along line 7-7.

The treatment of ruptured and unruptured intracranial aneurysms with the use of transluminally-delivered occlusive microcoils has a relatively low morbidity and mortality rate in comparison with surgical clipping. However, there are still many drawbacks that have been reported. Microcoils are typically delivered into the aneurysm one at a time, and it is of critical importance that each microcoil be visible, for example by fluoroscopy, and that if a microcoil is not delivered into a desirable position, that it may be safely and easily withdrawn from the aneurysm. A microcatheter is placed so that its tip is adjacent the neck of the aneurysm, and the microcoils are delivered through the lumen of the microcatheter. Microcatheter design, placement, and tip orientation are all important factors in determining how well the microcatheter will support the delivery, and if needed, removal, of the microcoil to and from the aneurysm. If excessive resistance is met during the delivery of the microcoil, the microcatheter may "back out", thus losing its stabilizing position and/or orientation in relation to the aneurysm. One complication that may occur during microcoil delivery or removal is the actual stretching of the winds of the microcoil. For example, if the microcoil is pulled into the microcatheter while the microcatheter is in a position that causes its tip to place a larger than desired force on a portion of the microcoil, the microcoil may not slide into the microcatheter easily, and an axially-directed tensile force may cause a significant and permanent increase in the length of the microcoil. The microcoil will then have permanently lost its mechanical characteristics and suffered from a decrease in radiopacity in the stretched area. Coil stretching of this nature can be expensive to the neurointerventionalist performing the procedure, as this microcoil will need to be discarded and replaced. But, it may also interfere with the procedure, as stretched coils may also be prone to being trapped, breaking, or inadvertently interlocking with other microcoils, already placed within the aneurysm. There is also the possibility of causing other microcoils that were already placed within the aneurysm to migrate out of the aneurysm, into the parent artery, a severe complication. A stretched microcoil that is partially within a multi-coil mass inside the aneurysm and partially within the microcatheter, and that cannot be further advanced or retracted, may necessitate an emergency craniotomy and very invasive microsurgical rescue procedure. Potential transcatheter methods for salvaging a stretched coil are less than desirable. They consist of either tacking the stretched coil to the inner wall of the parent artery with a stent, using a snare device to grasp and remove the stretched coil portion that is within the aneurysm, or placing the patient on long term antiplatelet therapy.

Placement of a first "framing" microcoil within an aneurysm is often done using a three-dimensional, or "complex", microcoil (a microcoil which is wound around a plurality of axes). The initial framing microcoil is the base structure into which later "filling" microcoils are packed. As the first microcoil placed into a completely uncoiled aneurysm, even if it is a three-dimensional or complex microcoil, the first loop of the microcoil may exit from the aneurysm after it has entered, instead of looping several times around the inside of the aneurysm. This is exacerbated by the absence of a prior microcoil, whose structure tends to help subsequently placed coils stay within the aneurysm. Microcoils in which all loops are formed at substantially the same diameter are especially prone to this exiting phenomenon when used as the first framing microcoil.

Microcoils may migrate out of the aneurysm either during the coiling procedure, or at a later date following the procedure. The migrated loop or loops of the microcoil can be a nidus for potentially fatal thromboembolism. The migration of portions of microcoils may be due to incomplete packing of the microcoil into the coil mass within the aneurysm.

Additionally, incomplete packing of microcoils, particularly at the neck of the aneurysm, may cause incomplete thrombosis, and thus leave the aneurysm prone to rupture, or in the case of previously ruptured aneurysms, re-rupture. Certain aneurysms with incomplete microcoil packing at the neck may nevertheless initially thrombose completely. However, they may still be prone to recanalization, via the dynamic characteristics of a thromboembolus. Compaction of the coil mass with the aneurysm is another factor which may cause recanalization. The inability to pack enough coil mass into the aneurysm, due to coil stiffness or shape is a possible reason for an insufficient coil mass.

Detachable microcoils are offered by several different manufacturers, using a variety of detachment systems. Though all detachment systems involve some dynamic process, some systems involve more physical movement of the system than others. Mechanical detachment systems, using pressure, unscrewing, or axial pistoning release, tend to cause a finite amount of movement of the implant at the aneurysm during detachment. In intracranial aneurysms, movement of this nature is undesirable. Any force which can potentially cause microcoil movement or migration should be avoided. Non-mechanical systems (chemical, temperature, electrolytic) have inherently less movement but often suffer from less consistency, for example, lacking a consistent short duration for a coil to detach. Though electrical isolation of the implant coil itself has aided in lower average coil detachment times, there is still some inconsistency in how quickly the coils will detach. In a larger aneurysm that might have ten or more coils implanted, the large or unpredictable detachment times are multiplied, and delay the procedure. Additionally, a single large detachment time may risk instability during the detachment, due to movement of the patient or the catheter system. Even systems that indicate that detachment has occurred, for example by the measurement of a current dropping below a certain threshold, are not completely trusted by users.

Many detachable microcoil systems include a detachment module (power supply, etc.) that is typically attached to an IV pole near the procedure table. There is usually a cable or conduit that connects the non-sterile module to the sterile microcoil implant and delivery wire. The attending interventionalist usually must ask a person in the room, who is not "scrubbed" for the procedure, to push the detach button on the module in order to cause the detachment to occur.

Most detachable systems have a particular structure at a junction between a pusher wire and the detachable coupled microcoil implant that is constructed in a manner allows the detachment to occur. Because of the need to have a secure coupling that allows repetitive insertion of the microcoil into the aneurysms and withdrawal into the microcatheter, many of these junctions have a physical structure that causes an increase in stiffness. Because this stiff section is immediately proximal to the microcoil being implanted, the implantation process can be negatively affected, sometimes causing the microcatheter to back out, and thus no longer provide sufficient support for the microcoil insertion. This is particularly true in aneurysms that are incorporated into a tortuous vascular anatomy.

FIG. 1 illustrates a vasoocclusive implant system 100 comprising microcoil implant 102 detachably coupled to a pusher member 104. The pusher member 104 includes a core wire 106, extending the length of the pusher member 104, and made from a biocompatible material such as stainless steel, for example 304 series stainless steel. The core wire 106 diameter at a proximal end 108 may be between 0.008" and 0.018", and more particularly between 0.010" and 0.012". An electrically insulated region 110 of the pusher member 104 extends a majority of the core wire 106 length, between a first point 112, approximately 10 cm from the extreme proximal end of the core wire 106 and a second point 114, near the distal end 116 of the core wire 106. Directly covering the surface of the core wire 106 is a polymeric coating 118, for example PTFE (polytetrafluoro ethylene), Parylene or polyimide, and having a thickness of about 0.00005" to about 0.0010", or more particularly 0.0001" to 0.0005". A polymeric cover tube 120 is secured over the core wire 106 and the polymeric coating 118. The polymeric cover tube 120 may comprise polyethylene terephthalate (PET) shrink tubing that is heat shrunk over the core wire 106 (and optionally, also over the polymeric coating 118) while maintaining a tension of the ends of the tubing. A marker coil 122 (FIG. 9) may be sandwiched between the core wire 106 and the polymeric cover tube 120, for example, by placing the marker coil 122 over the core wire 106 or over the polymeric coating 118, and heat shrinking or bonding the polymeric cover tube 120 over the them. The core wire 106 may have transition zones, including tapers, where the diameter decreases from its diameter at the proximal end 108 to a diameter of, for example, 0.005" to 0.006" throughout a portion of the electrically insulated region 110 of the pusher member 104. The diameter of the core wire 106 at the distal end 116 may be 0.002" to 0.003", including the portion of the distal end 116 that is outside of the electrically insulated region 110 of the pusher member 104. A tip 124 may be applied to the polymeric cover tube 120 in order to complete the electrically insulated region 110. This is described in more detail with relation to FIGS. 7-9. The section of polymeric cover tube 120 that covers the polymeric coating 118 is a redundant, and thus extremely reliable, electrical isolation of the core wire 106.

The pusher member 104 may have a length of about 175 cm to 180 cm, to allow access to a variety of intracranial aneurysms. The vasoocclusive implant system 100 is typically used with microcatheters having a length of between 135 cm and 150 cm, which may in turn be placed down diagnostic catheters or introducer sheaths having a length of between 90 cm and 100 cm. The microcoil implant 102 is detachably coupled to the pusher member 104 via a coupling joint 126, which is described in more detail with relation to FIG. 7. FIG. 3 illustrates a coil assembly 128 of the microcoil implant 102 (shortened for sake of easier depiction). An embolic coil 130 may be constructed of platinum or a platinum alloy, for example 92% platinum/8% Tungsten, and close wound from wire 144 having a diameter between 0.001" and 0.004", or more particularly between 0.00125" to 0.00325". The coil may have a length (when straight) of between 0.5 cm and 50 cm, or more particularly between 1 cm and 40 cm. Prior to its assembly into the microcoil implant 102, the embolic coil 130 is formed in to one of several possible shapes, as described in more detail in relation to FIGS. 4-6 and FIGS. 10A-10B. In order to minimize stretching of the embolic coil 130 of the microcoil implant 102, a tether 132 is tied between a proximal end 134 and a distal end 136 of the embolic coil 130. The tether 132 may be formed of a thermoplastic elastomer such as Engage®, or a polyester strand, such as diameter polyethylene terephthalate (PET). The diameter of the tether 132 may be 0.0015" to 0.0030", or more particularly about 0.0022" for the Engage strand. The diameter of the tether 132 may be 0.00075" to 0.0015", or more particularly about 0.0010" for the PET strand. The primary outer diameter of the embolic coil 130 may be between 0.009" and 0.019". In order to secure the tether at the proximal end 134 and distal end 136 of the embolic coil 130, a two reduced diameter portions 138, 140 are created in certain winds of the embolic coil 130, for example by carefully pinching and shaping with fine tweezers. The end 142 of the reduced diameter portion 140 is trimmed and the tether 132 is tied in one or more knots 147, 148, around the wire 144 of the reduced diameter portion 140. A tip encapsulation 146 comprising an adhesive or an epoxy, for example, an ultraviolet-curable adhesive, a urethane adhesive, a ready-mixed two-part epoxy, or a frozen and defrosted two-part epoxy, is applied, securing the one or more knots 147, 148 to the reduced diameter portion 140, and forming a substantially hemispherical tip 150. With a sufficient amount of slack/tension placed on the tether 132, the tether is tied in one or more knots 151, 152 to the reduced diameter portion 138. A cylindrical encapsulation 154, also comprising an adhesive or an epoxy, is applied, securing the one or more knots 151, 152 to the reduced diameter portion 138. The cylindrical encapsulation 154 provides electrical isolation of the embolic coil 130 from the core wire 106, and thus allows for a simpler geometry of the materials involved in the electrolysis during detachment. The tether 132 serves as a stretch-resistant member to minimize stretching of the embolic coil 130. In a separate embodiment, the tether 132 may be made from a multi-filar or stranded polymer or a microcable.

Turning again to FIG. 1, an introducer tube 155, having an inner lumen 156 with a diameter slightly larger than the maximum outer diameter of the microcoil implant 102 and pusher member 104 of the vasoocclusive implant system 100 is used to straighten a shaped embolic coil 130, and to insert the vasoocclusive implant system 100 into a lumen of a microcatheter. The vasoocclusive implant system 100 is packaged with and is handled outside of the patient's body within the inner lumen 156 of the introducer tube 155. As seen in FIG. 2, the vasoocclusive implant system 100 and introducer tube 155 are packaged for sterilization by placing them within a protective shipping tube 158. The proximal end 108 of the pusher member 104 is held axially secure by a soft clip 160.

FIGS. 4-6 illustrate vasoocclusive implants according to three different embodiments of the invention. FIG. 4 illustrates a framing microcoil implant 200 made from an embolic coil 201 and having a box shape which approximates a spheroid when placed within an aneurysm. Loops 202, 204, 206, 208, 210, 212 are wound on three axes: an X-axis extending in a negative direction (−X) and a positive direction (+X) from a coordinate origin (O), a Y-axis extending in a negative direction (−Y) and a positive direction (+Y) from the coordinate origin (O), and an Z-axis extending in a negative direction (−Z) and a positive direction (+Z) from the coordinate origin (O). A first loop 202 having a diameter $D_1$ begins at a first end 214 of the embolic coil 201 and extends around the +X-axis in a direction 216. As depicted in FIG. 4, the first loop 202 includes approximately 1½ revolutions, but may (along with the other loops 204, 206, 208, 210, 212) include between ½ revolution and 10 revolutions. The second loop 204 having a diameter $D_2$ continues from the first loop 202 and extends around the −Y-axis in a direction 218. The third loop 206 then extends around the +Z-axis in a direction 220. The fourth loop 208 then extends around the −X-axis in a direction 222. The fifth loop 210 then extends around the +Y-axis in a direction 224. And finally, the sixth loop 212 extends around the −Z-axis in a direction 226. As seen in FIG. 4, subsequent to the forming of the loops 202, 204, 206, 208, 210, 212, the coupling joint 126 is formed at a second end 228 of the embolic coil 201. This framing microcoil implant 200 is configured for being the initial microcoil placed within an aneurysm, and therefore, in this embodiment, loops 204, 206, 208, 210, and 212 all have a diameter approximately equal to $D_2$. The first loop 202, however, is configured to be the first loop introduced into the artery, and in order to maximize the ability of the microcoil implant 200 to stay within the aneurysm during coiling, the diameter $D_1$ of the first loop 202 is to between 65% and 75% of the diameter $D_2$, and more particularly, about 70% of the diameter of $D_2$. Assuming that $D_2$ is chosen to approximate the diameter of the aneurysm, when the first loop 202 of the microcoil implant 200 is inserted within the aneurysm, as it makes its way circumferentially around the wall of the aneurysm, it will undershoot the diameter of the aneurysm if and when it passes over the opening at the aneurysm neck, and thus will remain within the confined of the aneurysm. Additionally, the microcoil implant 200, when fully placed into an aneurysm as an initial framing microcoil, is likely to cross the open area at the aneurysm neck several times, thus creating good "neck coverage" which further aids keeping subsequently placed microcoils within the aneurysm. Upon assembly of the microcoil implant 200 into the vasoocclusive implant system 100, the choice of the tether 132 can be important for creating a microcoil implant 200 that behaves well as a framing microcoil, framing the aneurysm and creating a supportive lattice to aid subsequent coiling, both packing and finishing. For example, the tether 132 may be made from 0.0009" diameter PET thread in microcoil implants 200 having a diameter $D_2$ of 5 mm or less, while the tether 132 may be made from 0.0022" diameter Engage thread in microcoil implants 200 having a diameter $D_2$ of 5 mm or more. In addition, the diameter of the wire 144, if 92/8 Pt/W, may be chosen as 0.0015" in 0.011" diameter embolic coils 130 and 0.002" in 0.012" diameter embolic coils 130. The 0.011" embolic coils 130 may be chosen for the construction of microcoil implants 200 having a diameter $D_2$ of 4.5 mm or less, and the 0.012" diameter embolic coils 130 may be chosen for the construction of microcoil implants 200 having a diameter $D_2$ of 4.5 mm or more. In microcoil implants 200 having a diameter D2 of 6 mm or larger, additional framing microcoils may be constructed having 0.013" or larger embolic coils 130 wound with 0.002" and larger wire 144. It should be noted that the coiling procedure need not necessarily use only one framing microcoil, and that during the implantation procedure, one or more framing microcoils may be used to set up the aneurysm for filling microcoils and finishing microcoils. The microcoil implants 200 described may also be formed from embolic coils 130 having other diameters, for example a larger diameter such as 0.018". The range of diameters of embolic coils 130, provide an array of microcoil implants 200 that may be placed through the lumens of microcatheters having inner diameters of 0.016" to 0.021". A diameter range for the microcoil implants is contemplated to typically be between 2 mm and 15 mm.

Figure 10A:
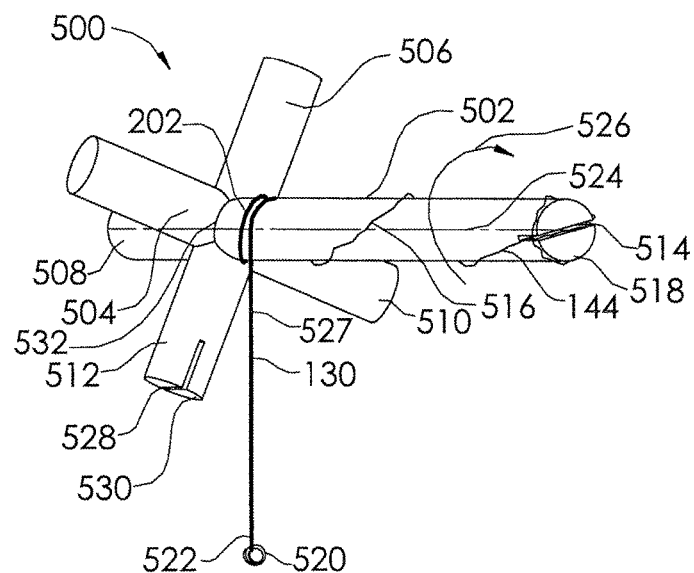
FIG. 10A-10B are a perspective view of a mandrel for forming a vasoocclusive implant according to an embodiment of the invention.

Turning to FIG. 10A, a mandrel 500 for forming a vasoocclusive implant has six arms 502, 504, 506, 508, 510, 512 which are used for creating the loops 202, 204, 206, 208, 210, 212 (respectively) of the microcoil implant 200 of FIG. 4. The first loop 202 is wound around a first arm 502, the second loop 204 is wound around a second arm 504, the third loop 206 is wound around a third arm 506, the fourth loop 208 is wound around a fourth arm 508, the fifth loop 210 is wound around a fifth arm 510, and a sixth loop 212 is wound around a sixth arm 512. The wire 144 of the embolic coil 130 is pulled into a straight extension 516 for a length at the first end 214 (FIG. 4) of the embolic coil 130, and is secured into a securing element 514 at an end 518 of the first arm 502. A weight 520 is attached to an extreme end 522 of the embolic coil 130 and the mandrel 500 is rotated in direction 526 with respect to the X-axis 524, causing the first loop 202 to be formed. Depending on the type and size of embolic coil 130 used, the weight 520 may range from between 0.75 grams and 9 grams. The position of the mandrel 500 is then adjusted prior to the forming of each consecutive loop, so that whichever arm/axis that the current loop is being formed upon is approximately parallel to the ground, with the weight 520 pulling an extending length 527 of the embolic coil 130 taut in a perpendicular direction to the floor (in the manner of a plumb line). When the forming of the microcoil implant 200 on the mandrel 500 is complete, the second end 228 (FIG. 4) is secured by stretching a length of the wire 144 and attaching it to a securing element 528 at an end 530 of arm 512. The formed loops 202, 204, 206, 208, 210, 212 of the microcoil implant 200 are now held securely on the mandrel 500, and the shape of the loops is set by placing them into a furnace, for example at 700° C. for 45 minutes. After cooling to room temperature, the formed loops of the microcoil implant 200 are carefully removed from the mandrel 500, and the rest of the manufacturing steps of the microcoil implant 200, 102 and vasoocclusive implant system 100 are performed. In the specific case of the microcoil implant 200, the diameter of the first arm 502 of the mandrel 500 is approximately 70% of the diameter of each of the other arms 504, 506, 508, 510, 512, in order to create a first loop 202 that is approximately 70% the diameter of the other loops 204, 206, 208, 210, 212.

FIG. 5 illustrates a filling microcoil implant 300 having a helical shape. The filling microcoil implant 300 is manufactured in a similar winding and setting technique as the framing microcoil implant 200, but the helical loops 302 of the filling microcoil implant 300 are wound on a single cylindrical mandrel (not shown). The framing microcoil implant 200 is formed from an embolic coil 130 having a first end 314 and a second end 328. The tether 132 (FIG. 3) of the filling microcoil implant 300 can be constructed from a variety of materials, including a thermoplastic elastomer such as Engage. The diameter of the tether 132 formed from Engage may range from 0.002" to 0.00275" and more particularly, may be about 0.0022". The wire 144 used in making the embolic coil 130 used to construct the filling microcoil implant 300 may be 92/8 Pt/W wire of a diameter between about 0.00175" and 0.00275", and more particularly between 0.002" and 0.00225". The outer diameter of the embolic coil 130 of the filling microcoil implant 300 may be between 0.011" and 0.013", more particularly about 0.012". One or more filling microcoil implants 300 can be used after one or more framing coil implants 200 have been placed in the aneurysm, to pack and fill as much volume of the aneurysm as possible. The comparatively soft nature of the filling microcoil implants 300 allows a sufficient amount of packing to achieve good thrombosis and occlusion, without creating potentially dangerous stresses on the wall of the aneurysm that could potentially lead to rupture (or re-rupture). A variety of tether 132 diameters and materials, as well as a variety of wire 144 diameters, allow for quite a range of implant stiffnesses, and thus a variable softness profile, to match the particular clinical situation. A variety of embolic coil 130 lengths for each diameter size further provides a range in the effect of the implant of the aneurysm wall. In addition to the use of a helically shaped microcoil as a filling microcoil implant 300, they may also be used as a finishing microcoil implant, which is the last one or more implants that are placed at the neck of the aneurysm to engage well with the coil mass while maximizing the filled volume at the neck of the aneurysm. These finishing microcoils may have an outer diameter of about 0.010", and may be wound from 92/8 Pt/W wire having a diameter of between 0.001" to 0.00175", more particularly between 0.00125" and 0.0015". The tether 132 used in a helical finishing microcoil may comprise 0.001" PET thread.

FIG. 6 illustrates a complex microcoil implant 400, having a first loop 402, second loop 404, third loop 406, fourth loop 408, fifth loop 410, and sixth loop 412, wound in three axes, much like the microcoil implant 200 of FIG. 4. However, the Diameter $D_3$ of the first loop 402 is about the same as the diameter $D_4$ of each of the other loops 404, 406, 408, 410, 412. Therefore the mandrel 500 used in the construction of the loops 402, 404, 406, 408, 410, 412 would include a first arm 502 having a similar diameter to the other arms 504, 506, 508, 510, 512. A complex microcoil implant 400 of this construction may be used as a framing microcoil implant, but may alternatively by used as a finishing microcoil implant. The complex or three-dimensional structure in many clinical situations can aid in better engagement of the finishing microcoil implant with the rest of the coil mass, due to its ability to interlock. There is thus less chance of the finishing microcoil implant migrating out of the aneurysm, into the parent artery.

Figure 10B:
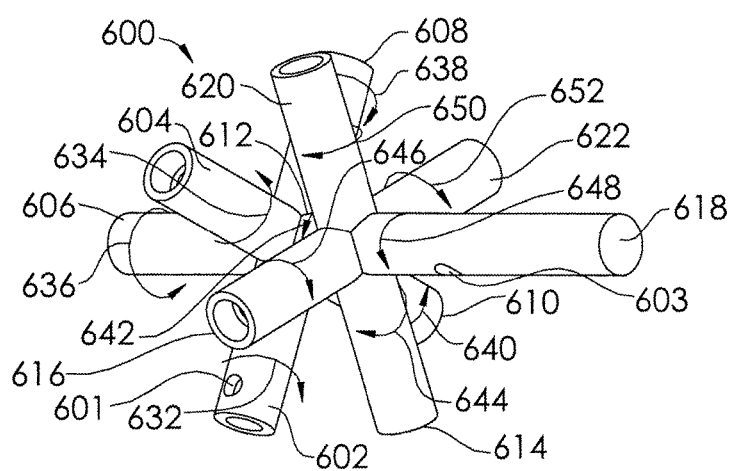

Complex microcoil implants 400 may be formed with a variety of different diameters $D_4$ and each of the six loops 402, 404, 406, 408, 410, 412 may include varying numbers of revolutions. For example, a complex microcoil implant 400 may be formed such that the first loop 402 has more than four complete revolutions, and the second loop 404 has fewer than two complete revolutions, and any number of other combinations. When a relatively large diameter $D_4$ is chosen and when a relatively large number of revolutions are formed, the total length of the embolic coil 130 can become quite large, sometimes even 40 cm or more in length. It is often desired to form a complex microcoil implant 400 (or framing microcoil implant 200) with a large number of loops in order to maximize the embolic mass, and for this reason, sometimes a tool such as the mandrel 500 may become limiting. For example, winding too many revolutions of a loop around the sixth arm 512, may move some of the latter revolutions too far from an origin or center point 532 of the mandrel 500, and towards the end 530. This might result in a complex microcoil implant 400 that does not fill an aneurysm as a cohesive unit. It also may be prone to migration from the aneurysm. A mandrel 600 is illustrated in FIG. 10B which allows for the forming of a complex microcoil implant 400 that has a larger number of revolutions on each loop, while also maintaining a form in which the loops maintain a cohesive unit. A complex microcoil implant 400 having a larger number of rotations per loop is wound on the mandrel 600 in the same manner as described with mandrel 500 of FIG. 10A, but an additional set of arms and winding areas allow for a more centered and controlled winding procedure. The complex microcoil implant 400 having the longer length can be wound on the mandrel 600 in the following order. The stretched end of the wire 144 of the embolic coil 130 is secured within a hole 601 in a first arm 602 of the mandrel 600. For example, the wire 144 may be secured with an interference pin or the equivalent. A first loop is wound around the first arm 602 in a first direction 632 for a desired number of revolutions. A second loop is wound around a second arm 604 in a second direction 634 for a desired number of revolutions. A third loop is wound around a third arm 606 in a third direction 636. A fourth loop is wound around a fourth arm 608 in a fourth direction 638. A fifth loop is wound around a fifth arm 610 in a fifth direction 640. A sixth loop is wound around a cylindrical junction 612 in a sixth direction 642. The cylindrical junction 612 is directly interposed between arms 602, 604, 608, 610 and arms 614, 616, 620, 622. The cylindrical junction 612 serves as a sixth arm, and extends along the same axis as the arm 606 and an arm 618. A seventh loop is wound around a seventh arm 614 in a seventh direction 644. An eighth loop is wound around an eighth arm 616 in an eighth direction 646. A ninth loop is wound around the ninth arm 618 in a ninth direction 648. A tenth loop is wound around a tenth arm 620 in a tenth direction 650. And finally, an eleventh loop is wound around an eleventh arm 622 in an eleventh direction 652. Another stretched end of the embolic coil 130 may be secured in another hole (not visible) in the eleventh arm 622. The complex microcoil implant 400 having a longer length is then heat set as previously described. Thus, by using this efficient arm configuration for the winding of the loops, a longer length complex microcoil implant 400 is provided which has superior shape retention. Complex microcoil implants 400 may also be made which do not have all of the eleven loops described in relation to the mandrel 600. For example, a complex microcoil implant 400 may be made with a process which does not use the tenth and eleventh arms 620, 622, instead terminating the winding by securing a stretched end of the embolic coil 130 in a hole 603 in the ninth arm 618.

FIG. 7 illustrates the coupling joint 126, the tip 124 of the vasoocclusive implant system 100 of FIG. 1, and a detachment zone 162 between the tip 124 and the coupling joint 126. The detachment zone 162 is the only portion of the core wire 106 other than the proximal end 108 (FIG. 1) that is not covered with the electrically insulated region 110, and the only one of the two non-insulated portions of the core wire 106 that is configured to be placed within the bloodstream of the patient. Thus, as described in accordance with FIGS. 7-9, the detachment zone 162 is the sacrificial portion of the vasoocclusive implant system 100 that allows the microcoil implant 102 to be detached from the pusher member 104. The tether 132, the embolic coil 130 (not pictured) and the core wire 106 are coupled together with a coupler coil 166 and a potted section 164, for example UV adhesive or other adhesives or epoxy. The coupler coil 166 made me made from 0.001" to 0.002" diameter platinum/tungsten (92%/8%) wire and have an outer diameter of 0.006" to 0.009", or more particularly, 0.007" to 0.008". The coupler coil 166 may be attached to the core wire 106 with solder, such as silver solder or gold solder. When using PET shrink tubing as the polymeric cover tube 120, an initial detachment zone length $L_i$ of approximately 0.015" can be achieved. The tip 124 may then be formed, for example by application of UV adhesive and subsequent UV-curing, so that the finished detachment zone length $L_f$ is between 0.002" and 0.008". By careful application of the UV adhesive under the microscope followed by curing with a UV light source, a finished detachment zone length $L_f$ between 0.002" and 0.003" may be achieved.

Figure 8:
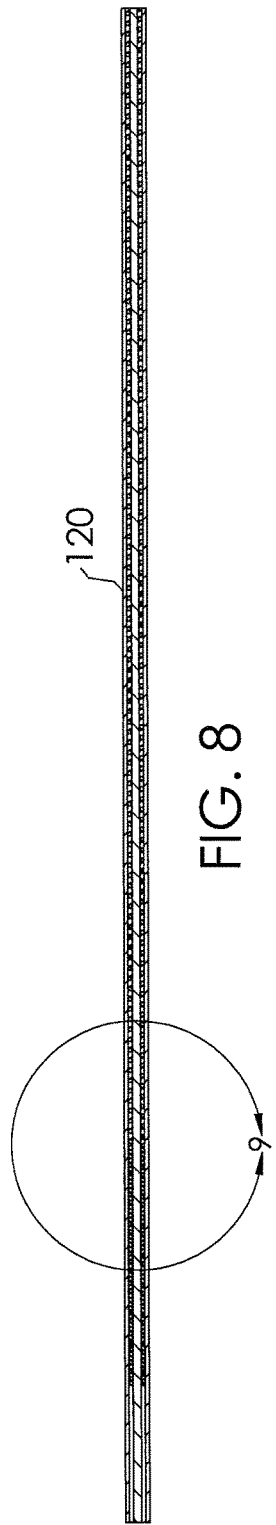
FIG. 8 is a sectional view of FIG. 1, taken along line 8-8.
Figure 9:
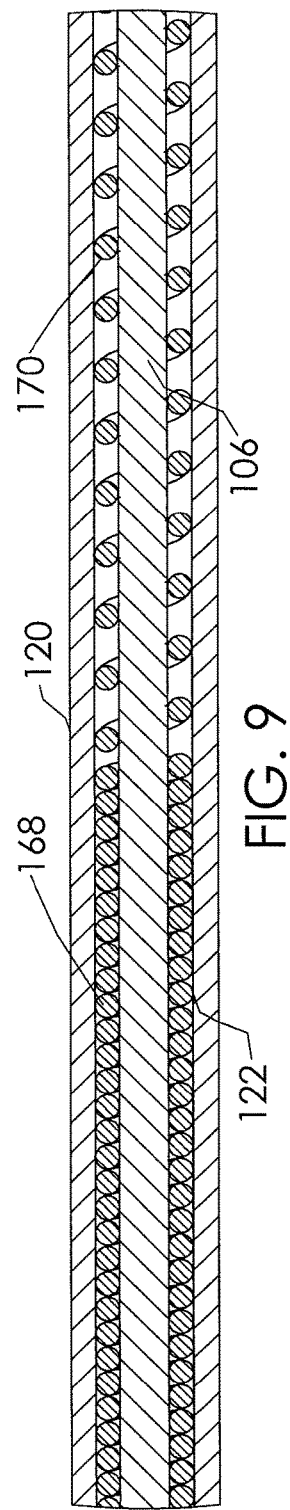
FIG. 9 is a detailed view of a transition portion of the vasoocclusive implant system depicted in FIG. 8, taken from within circle 9.

FIGS. 8 and 9 illustrate a section of the pusher member 104 approximate 3 cm proximal to the detachment zone 162. A marker coil 122 comprising a close wound portion 168 and a stretched portion 170 (extending distally) is sandwiched between the core wire 106 and the polymeric cover tube 120. The marker coil 122 may be constructed from 0.002" diameter platinum/tungsten (92%/8%) wire and have an outer diameter of 0.008". The close wound portion 168 is more radiopaque than the stretched portion 170, and thus is used as a visual guide to assure that the detachment zone 162 is just outside of the microcatheter during the detachment process. The marker coil 122 may be attached to the core wire 106 with solder, such as silver solder or gold solder.

Figure 11:
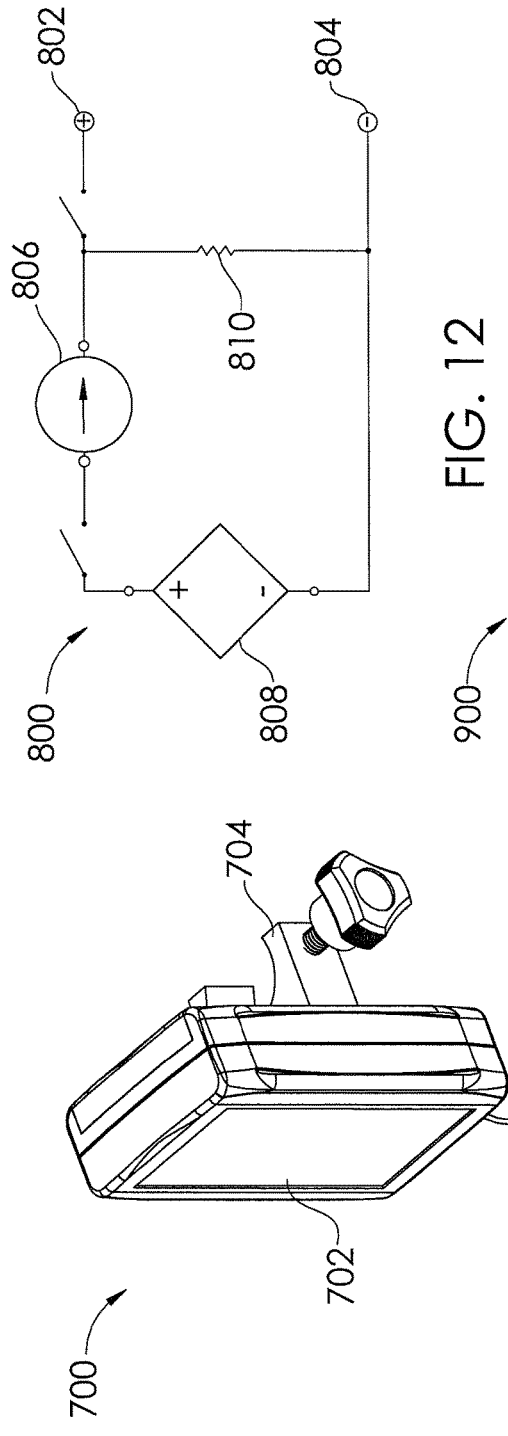
FIG. 11 is a perspective view of an electrical power supply configured to electrically couple to an electrolytically detachable implant assembly.

FIG. 11 illustrates an electrical power supply 700 for electrically coupling to the vasoocclusive implant assembly 100 of FIG. 1. The electrical power supply 700 comprises a battery-powered power supply module 702 having a pole clamp 704, for attaching to an IV pole, and a control module 706. The control module 706 includes an on/off button 716 and first and second electrical clips 712, 714, providing first and second electrodes 708, 710. The control module 706 is electrically connected to the power supply module 702 via an electrical cable 718, and the first and second electrical clips 712, 714 are each connected to the control module 706 via insulated electrical wires 720, 722.

Figure 12:
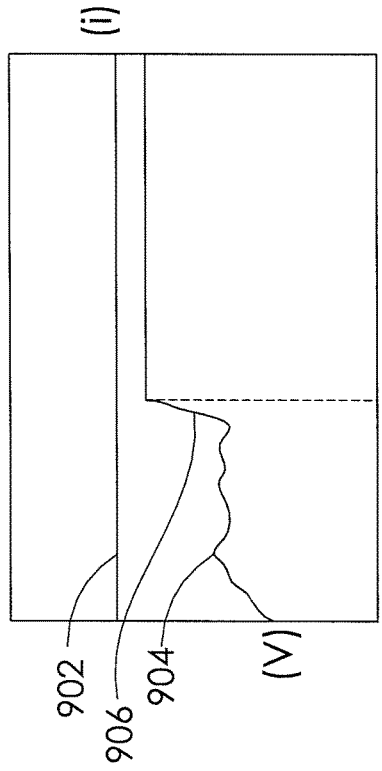
FIG. 12 is a circuit diagram of the electrical power supply coupled to an electrolytically detachable implant assembly that is inserted within a patient.
Figure 13:
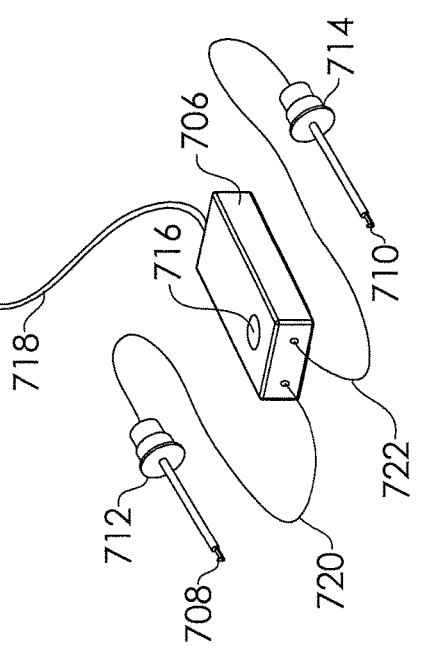
FIG. 13 is a graphical illustration of electrical characteristics of the electrical power supply over time during the detachment of an electrically detachable implant.

Turning to FIG. 12, in a circuit diagram 800 of the electrical power supply 700 of FIG. 11, the electrode 708 is positively charged and is represented by a terminal connection 802, at which the first electrode 708 of the first clip 712 is connected to the uninsulated proximal end 108 of the core wire 106 of the pusher member 104 (FIG. 1). The electrode 710 is negatively charged and is represented by a terminal connection 804, at which the second electrode 710 of the second clip 714 is connected to a conductive needle or probe, whose tip is inserted into the patient, for example at the groin or shoulder areas. A constant current source 806 powered by a controlled DC voltage source 808 is run through a system resistor 810 and the parallel resistance in the patient, current passing through the core wire 106 and the patient, via the uninsulated detachment zone 162 (FIG. 7). As shown in the graph 900 in FIG. 13, a constant current (i) 902 is maintained over time (t), with the controlled DC voltage source 808 increasing the voltage 904 as the total resistance increases due to the electrolytic dissolution of the stainless steel at the detachment zone 162. When the detachment zone 162 is completely obliterated, the voltage 904 is forced upward in a spike 906, triggering a notification of detachment. An LED may be included as part of the electrical power supply 700 in order to indicate either that detachment is taking place, or alternatively that detachment has been completed.

Figure 14:
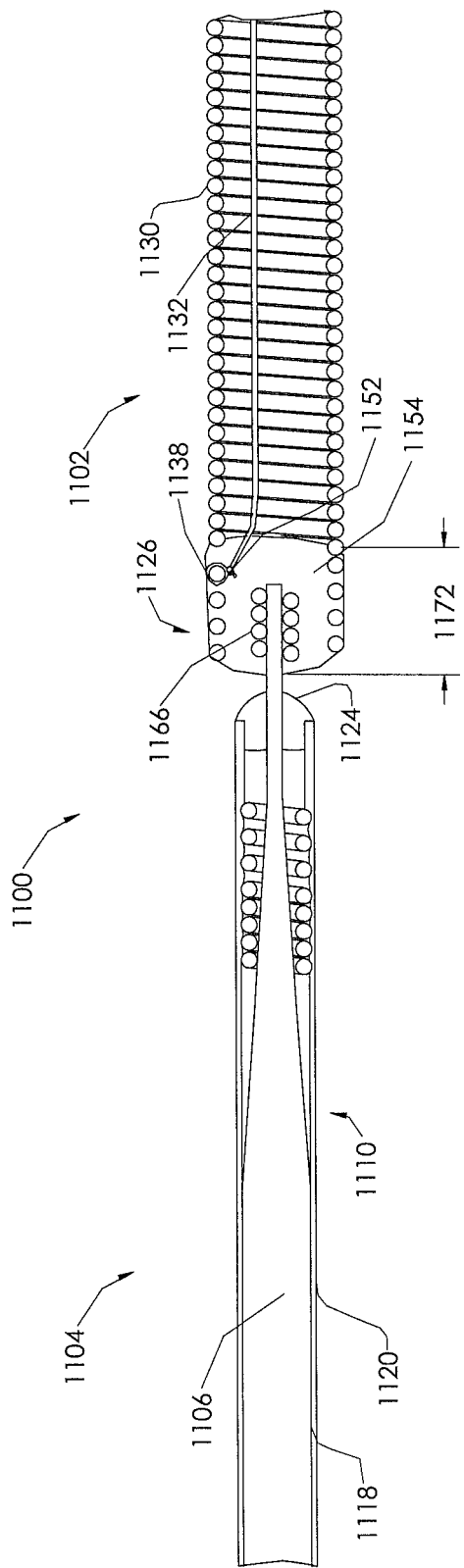
FIG. 14 is a sectional view of a vasoocclusive implant system having a decreased stiffness at a region near the detachment zone.

FIG. 14 illustrates a vasoocclusive implant system 1100 comprising a microcoil implant 1102 detachably coupled to a pusher member 1104, including a stainless steel core wire 1106 coated with a polymeric coating 1118 and covered with a polymeric cover tube 1120. The polymeric coating 1118, polymeric cover tube 1120, and a tip 1124, formed of an adhesive of epoxy, constitute an electrically insulated region 1110. The vasoocclusive implant system 1100 is similar to the vasoocclusive implant system 100 of FIG. 1, except for a modified construction at a coupling joint 1126 where the microcoil implant 1102 and the pushed member 1104 are coupled together, as depicted in FIG. 14. A tether 1132 is tied in a knot 1152 to a reduced diameter portion 1138 of an embolic coil 1130. A coupler coil 1166 is attached to the core wire 1106 and inserted inside the embolic coil 1130 in a coaxial configuration. A cylindrical encapsulation 1154 is applied (for example with a UV adhesive) to join the core wire 1106, coupler coil 1166, embolic coil 1130 and tether 1132 together. The cylindrical encapsulation 1154 provides electrical isolation of the embolic coil 1130 from the core wire 1106, and thus allows for a simpler geometry of the materials involved in the electrolysis during detachment. This coaxial arrangement creates a stiff zone 1172 that is significantly shorter than prior art stiff (non-bendable) zones, which are often greater than 0.040" in length. Using this coaxial arrangement, a stiff zone of between 0.015" and 0.030" can be created, and more particularly, between 0.020" and 0.025". This creates significantly increased flexibility of the microcoil implant 1102 as it is being delivered into an aneurysm from a microcatheter, and is much less likely to cause the microcatheter to lose its position at the neck of the aneurysm ("kickback"). In turn, the stability of the microcatheter for supporting the insertion of the microcoil implant 1102 is improved.

FIGS. 15A through 15G illustrate use of the vasoocclusive implant system of FIG. 1 to implant a microcoil implant 16. Prior to implantation, the coil is coupled to the pusher member 14 as illustrated in FIG. 1.

A microcatheter 12 is introduced into the vasculature using a percutaneous access point, and it is advanced to the cerebral vasculature. A guide catheter and/or guide wire may be used to facilitate advancement of the microcatheter 12. The microcatheter 12 is advanced until its distal end is positioned at the aneurysm A, as seen in FIG. 15A.

The microcoil implant 16 is advanced through the microcatheter 12 to the aneurysm A, as seen in FIG. 15B. A continuous flush of normal saline may be provided via a pressurized bag, for example at a pressure of 300 mm Hg. The continuous flush helps to decrease friction between the microcoil implant 16 and the lumen of the microcatheter 12, and may also serve to reduce the possibility of clot formation. The microcoil implant 16 and the pusher member 14 may be pre-positioned within the microcatheter 12 prior to introduction of the microcatheter 12 into the vasculature, or they may be passed into the proximal opening of the microcatheter lumen after the microcatheter 12 has been positioned within the body. The pusher member 14 is advanced within the microcatheter 12 to deploy the microcoil implant 16 from the microcatheter 12 into the aneurysm A. As the microcoil implant 16 exits the microcatheter 12, it assumes its secondary shape as shown in FIG. 15C.

The microcoil implant 16 is positioned so that the detachment zone (162 in FIG. 7) is positioned just outside of the microcatheter 12, as seen in FIG. 15D. In order to achieve this, a slight introduction force may be placed on the pusher member 14 while slight traction is applied on the microcatheter 12. The microcoil implant 16 is then electrolytically detached from the pusher member 14, as seen in FIG. 15E, and the pusher member 14 is removed from the microcatheter, as seen in FIG. 15F.

If additional microcoil implants 16 are to be implanted, the steps of FIGS. 15B through 15F are repeated. The method is repeated for each additional microcoil implant 16 need to sufficiently fill the aneurysm A. Once the aneurysm is fully occluded, the microcatheter 12 is removed, as seen in FIG. 15G.

Figure 16A:
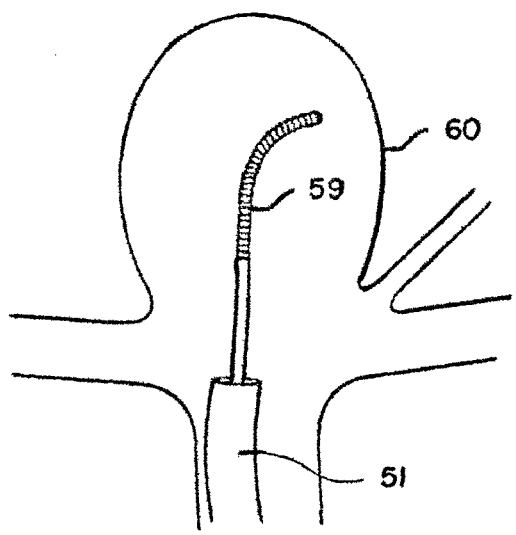
FIGS. 16A-16C show deployment sequences of occluding and aneurysm with an expandable flow disruptor device making use of certain embodiments of the electrolytic detachment system of the vasoocclusive implant systems of FIGS. 1-14.
Figure 16B:
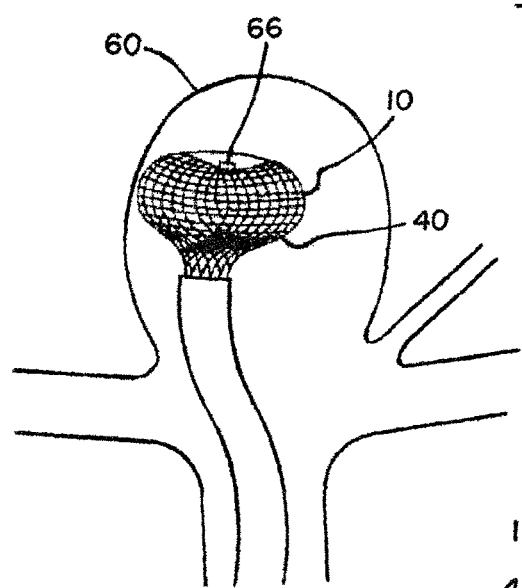
Figure 16C:
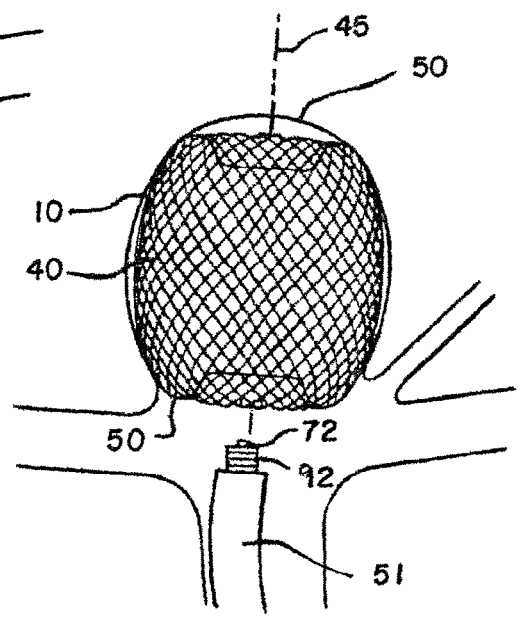

FIGS. 16A-16C show a deployment sequence of occluding an aneurysm using an expandable flow disruptor device making use of certain embodiments of the electrolytic detachment system of the vasoocclusive implant systems of FIGS. 1-14. Delivery and deployment of the implant device 10 discussed herein may be carried out by first compressing the implant device 10, or any other suitable implantable medical device for treatment of a patient's vasculature as discussed above. While disposed within a microcatheter 51 or other suitable delivery device, filamentary elements of layers 40 may take on an elongated, non-everted configuration substantially parallel to each other and to a longitudinal axis of the microcatheter 51. Once the implant device 10 is pushed out of the distal port of the microcatheter 51, or the radial constraint is otherwise removed, the distal ends of the filamentary elements may then axially contract towards each other, so as to assume the globular everted configuration within the vascular defect 60 (e.g. aneurysm) as shown in FIG. 16B. The implant device 10 may then be delivered to a desired treatment site while disposed within the microcatheter 51, and then ejected or otherwise deployed from a distal end of the microcatheter 51. In other method embodiments, the microcatheter 51 may first be navigated to a desired treatment site over a guidewire 59 or by other suitable navigation techniques. The distal end of the microcatheter 51 may be positioned such that a distal port of the microcatheter 51 is directed towards or disposed within a vascular defect 60 to be treated and the guidewire 59 withdrawn. The implant device 10 secured to the delivery apparatus 92 (e.g. pusher member) may then be radially constrained, inserted into a proximal portion of the inner lumen of the microcatheter 51, and distally advanced to the vascular defect 60 through the inner lumen. Once the distal tip or deployment port of the delivery system is positioned in a desirable location adjacent or within a vascular defect, the implant device 10 may be deployed out of the distal end of the microcatheter 51, thus allowing the device to begin to radially expand as shown in FIG. 16C. As the implant device 10 emerges from the distal end of the delivery apparatus 92 or microcatheter 51, the implant device 10 may start to expand to an expanded state within the vascular defect 60, but may be at least partially constrained by an interior surface of the vascular defect 60. At this time the implant device 10 may be detached from the delivery apparatus 92.

Vasoocclusive implants systems may be used to block blood vessels, in additional to their use in the embolization of aneurysms. A variety of other vascular implants may make use of certain embodiments of the electrolytic detachment system of the vasoocclusive implant systems of FIGS. 1-14. For example, a variety of tubular implants, such as stents or tubular flow diversion implants may be implanted to occlude an artery on their own, or in combination with embolic microcoils or liquid embolics. Stent grafts may be implanted, for example in an aneurysm of the abdominal aorta, which incorporate the detachment system of the present invention. Aneurysm neck-blocking implants which incorporate the detachment system of the present invention may also be implanted.

Figure 17:
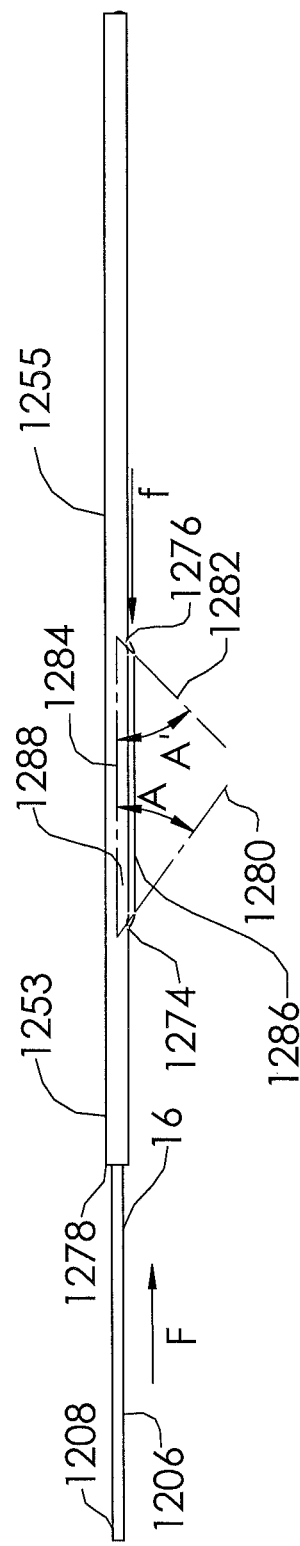
FIG. 17 is a side view of an introducer for use with a microcoil implant or other implant device.

FIG. 17 illustrates the proximal end 1253 of an introducer 1255 for aiding the insertion of a microcoil implant 16 or other implant device. A core wire 1206 of the microcoil implant 16 includes a proximal end 1208, which extends from the proximal end 1253 of the introducer 1255. A first side hole 1274 and a second side hole 1276 are placed in the wall 1278 of the introducer 1255, each having a diameter larger than the diameter of the core wire 1206. Each side hole 1274, 1276 may be made along a hole axis 1280, 1282 that is angled in relation to the introducer axis 1284. For example, where each angle A and A' is approximately 45°. A portion 1286 of the core wire 1206 exits from the first side hole 1274 and enters into the second side hole 1276. The frictional force (f) between the portion 1288 of the core wire 1206, and the outer surface 1288 and side holes 1274, 1276 of the introducer 1255, serves to maintain the microcoil implant 16 and core wire 1206 axially static in relation to the introducer 1255. This aids the maintenance of the packaged product, for example, during shipping. During insertion of the microcoil implant 16 into the microcatheter 12 and into the patient, an insertion force (F) may be stabilized by the frictional force (f), for example, giving the physician better feel while inserting with slow, precise motions.

What is claimed is:

1. A vasoocclusive implant comprising:
a metallic wire having a proximal end and a distal end and configured to transition from a constrained, deliverable configuration to a deployed, expanded configuration for the treatment of a vascular abnormality;
wherein, when in the constrained configuration, the metallic wire forms an elongate structure for delivery to a target site; and
wherein, upon delivery of the elongate helical coil structure to the target site, the metallic wire is configured to transition from the constrained configuration to the deployed configuration to form a three-dimensional structure for the treatment of the vascular abnormality, wherein the three-dimensional structure comprises a plurality of loops providing a multi-faceted and multi-angular outer surface configured to engage the vascular abnormality;
wherein the three-dimensional structure comprises:
a first loop having a first diameter and a second loop having a second diameter, the first and second loops generally arrayed along a first axis and spaced apart from each other by at least a dimension equal to the first diameter;
a third loop having a third diameter and a fourth loop having a fourth diameter, the third and fourth loops generally arrayed along a second axis and spaced apart from each other by at least a dimension equal to the third diameter; and
a fifth loop having a fifth diameter and a sixth loop having a sixth diameter, the fifth and sixth loops generally arrayed along a third axis and spaced apart from each other by at least a dimension equal to the fifth diameter;
wherein the first, second and third axes substantially approximate orthogonal lines, and
wherein the sixth diameter is between about 60% and 80% of the diameter of each of the first through fifth loop diameters.

2. A vasoocclusive implant comprising:
a metallic wire having a proximal end and a distal end and configured to transition from a constrained, deliverable configuration to a deployed, expanded configuration for the treatment of a vascular abnormality;
wherein, when in the constrained configuration, the metallic wire forms an elongate structure for delivery to a target site; and
wherein, upon delivery of the elongate helical coil structure to the target site, the metallic wire is configured to transition from the constrained configuration to the deployed configuration to form a three-dimensional structure for the treatment of the vascular abnormality, wherein the three-dimensional structure comprises a plurality of loops providing a multi-faceted and multi-angular outer surface configured to engage the vascular abnormality;
wherein the three-dimensional structure comprises:
a first loop having a first diameter and a second loop having a second diameter, the first and second loops generally arrayed along a first axis and spaced apart from each other by at least a dimension equal to the first diameter;

a third loop having a third diameter and a fourth loop having a fourth diameter, the third and fourth loops generally arrayed along a second axis and spaced apart from each other by at least a dimension equal to the third diameter; and a fifth loop having a fifth diameter and a sixth loop having a sixth diameter, the fifth and sixth loops generally arrayed along a third axis and spaced apart from each other by at least a dimension equal to the fifth diameter;

wherein the first, second and third axes substantially approximate orthogonal lines, and wherein the sixth diameter is between about 60% and 80% of the diameter of each of the first through fifth loop diameters, and wherein the first loop includes the first end of the metallic coil and the sixth loop includes the second end of the metallic coil.

3. A vasoocclusive implant comprising:

a metallic wire having a proximal end and a distal end and configured to transition from a constrained, deliverable configuration to a deployed, expanded configuration for the treatment of a vascular abnormality;

wherein, when in the constrained configuration, the metallic wire forms an elongate structure for delivery to a target site; and wherein, upon delivery of the elongate helical coil structure to the target site, the metallic wire is configured to transition from the constrained configuration to the deployed configuration to form a three-dimensional structure for the treatment of the vascular abnormality, wherein the three-dimensional structure comprises a plurality of loops providing a multi-faceted and multi-angular outer surface configured to engage the vascular abnormality;

wherein the three-dimensional structure comprises:

a first loop having a first diameter and a second loop having a second diameter, the first and second loops generally arrayed along a first axis and spaced apart from each other by at least a dimension equal to the first diameter;

a third loop having a third diameter and a fourth loop having a fourth diameter, the third and fourth loops generally arrayed along a second axis and spaced apart from each other by at least a dimension equal to the third diameter; and a fifth loop having a fifth diameter and a sixth loop having a sixth diameter, the fifth and sixth loops generally arrayed along a third axis and spaced apart from each other by at least a dimension equal to the fifth diameter;

wherein the first, second and third axes substantially approximate orthogonal lines, and wherein the sixth diameter is between about 60% and 80% of the diameter of each of the first through fifth loop diameters, and wherein the first loop includes the first end of the metallic coil and the sixth loop includes the second end of the metallic coil; and wherein the three-dimensional structure approximates a spheroid.

4. A vasoocclusive implant system comprising:

an elongate pushing member; and a vasoocclusive implant comprising a metallic wire having a proximal end and a distal end, the implant coupled to the elongate pushing member via a detachable zone at the proximal end of the metallic wire, the metallic wire configured to transition from a constrained, deliverable configuration to a deployed, expanded configuration for the treatment of a vascular abnormality;

wherein, when in the constrained configuration, the metallic wire forms an elongate structure for delivery to a target site; and wherein, upon delivery of the elongate helical coil structure to the target site a, the metallic wire is configured to transition from the constrained configuration to the deployed configuration to form a three-dimensional structure for the treatment of the vascular abnormality; wherein the three-dimensional structure comprises a plurality of loops providing a multi-faceted and multi-angular outer surface configured to engage the vascular abnormality and wherein the three-dimensional structure comprises:

a first loop having a first diameter and a second loop having a second diameter, the first and second loops generally arrayed along a first axis and spaced apart from each other by at least a dimension equal to the first diameter;

a third loop having a third diameter and a fourth loop having a fourth diameter, the third and fourth loops generally arrayed along a second axis and spaced apart from each other by at least a dimension equal to the third diameter; and a fifth loop having a fifth diameter and a sixth loop having a sixth diameter, the fifth and sixth loops generally arrayed along a third axis and spaced apart from each other by at least a dimension equal to the fifth diameter;

wherein the first, second and third axes substantially approximate orthogonal lines, and wherein the sixth diameter is between about 60% and 80% of the diameter of each of the first through fifth loop diameters.

5. A vasoocclusive implant system comprising:

an elongate pushing member; and a vasoocclusive implant comprising a metallic wire having a proximal end and a distal end, the implant coupled to the elongate pushing member via a detachable zone at the proximal end of the metallic wire, the metallic wire configured to transition from a constrained, deliverable configuration to a deployed, expanded configuration for the treatment of a vascular abnormality;

wherein, when in the constrained configuration, the metallic wire forms an elongate structure for delivery to a target site; and wherein, upon delivery of the elongate helical coil structure to the target site a, the metallic wire is configured to transition from the constrained configuration to the deployed configuration to form a three-dimensional structure for the treatment of the vascular abnormality; wherein the three-dimensional structure comprises a plurality of loops providing a multi-faceted and multi-angular outer surface configured to engage the vascular abnormality and wherein the three-dimensional structure comprises:

a first loop having a first diameter and a second loop having a second diameter, the first and second loops generally arrayed along a first axis and spaced apart from each other by at least a dimension equal to the first diameter a third loop having a third diameter and a fourth loop having a fourth diameter, the third and fourth loops generally arrayed along a second axis and spaced apart from each other by at least a dimension equal to the third diameter; and a fifth loop having a fifth diameter and a sixth loop having a sixth diameter; the fifth and sixth loops generally arrayed along a third axis and spaced apart from each other by at least a dimension equal to the fifth diameter;

wherein the first, second and third axes substantially approximate orthogonal lines, and wherein the sixth diameter is between about 60% and 80% of the diameter of each of the first through fifth loop diameters;

wherein the first loop includes the first end of the metallic coil and the sixth loop includes the second end of the metallic coil.

6. A vasoocclusive implant system comprising:

an elongate pushing member; and a vasoocclusive implant comprising a metallic wire having a proximal end and a distal end, the implant coupled to the elongate pushing member via a detachable zone at the proximal end of the metallic wire, the metallic wire configured to transition from a constrained, deliverable configuration to a deployed, expanded configuration for the treatment of a vascular abnormality;

wherein, when in the constrained configuration, the metallic wire forms an elongate structure for delivery to a target site; and wherein, upon delivery of the elongate helical coil structure to the target site a, the metallic wire is configured to transition from the constrained configuration to the deployed configuration to form a three-dimensional structure for the treatment of the vascular abnormality;

wherein the three-dimensional structure comprises a plurality of loops providing a multi-faceted and multi-angular outer surface configured to engage the vascular abnormality and wherein the three-dimensional structure comprises:

a first loop having a first diameter and a second loop having a second diameter, the first and second loops generally arrayed along a first axis and spaced apart from each other by at least a dimension equal to the first diameter;

a third loop having a third diameter and a fourth loop having a fourth diameter, the third and fourth loops generally arrayed along a second axis and spaced apart from each other by at least a dimension equal to the third diameter; and a fifth loop having a fifth diameter and a sixth loop having a sixth diameter; the fifth and sixth loops generally arrayed along a third axis and spaced apart from each other by at least a dimension equal to the fifth diameter;

wherein the first, second and third axes substantially approximate orthogonal lines, and wherein the sixth diameter is between about 60% and 80% of the diameter of each of the first through fifth loop diameters;

and, wherein the three-dimensional structure approximates a spheroid.

* * * * *